(12) United States Patent
Moore

(10) Patent No.: US 6,889,087 B2
(45) Date of Patent: May 3, 2005

(54) SWITCHED REACTANCE MODULATED E-CLASS OSCILLATOR DESIGN

(75) Inventor: William Henry Moore, Canoga Park, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 440 days.

(21) Appl. No.: 10/180,882

(22) Filed: Jun. 26, 2002

(65) Prior Publication Data

US 2002/0165584 A1 Nov. 7, 2002

Related U.S. Application Data

(63) Continuation-in-part of application No. 09/973,486, filed on Oct. 5, 2001.
(60) Provisional application No. 60/238,488, filed on Oct. 6, 2000.

(51) Int. Cl.[7] .................................................. A61N 1/00
(52) U.S. Cl. ........................................................ 607/60
(58) Field of Search ........................ 607/30–32, 59–61; 331/1 R–187; 455/127, 116

(56) References Cited

U.S. PATENT DOCUMENTS

| | | |
|---|---|---|
| 3,617,646 A | 11/1971 | Knollman |
| 3,682,160 A | 8/1972 | Murata |
| 3,995,234 A | 11/1976 | Tuccinardi |
| 4,218,772 A | 8/1980 | Sielman et al. |
| 4,245,178 A | 1/1981 | Justice |
| 4,321,706 A | 3/1982 | Craft |
| 4,539,531 A | 9/1985 | Thomas et al. |
| 4,553,110 A | 11/1985 | Kleinberg |
| 4,553,882 A | 11/1985 | Knappertz |
| 4,596,022 A | 6/1986 | Stoner |

(Continued)

OTHER PUBLICATIONS

Loeb et al. "Design and Fabrication of Hermetic Microelectronic Implants", Alfred E. Mann Institute for Biomedical Engineering, University of Southern California, (Oct. 12, 2000), presented at Microtechnology Conference, Lyons, France.

Nardin, Mark D., A Programmable Multichannel Microstimulator with Bi–Directional Telemetry, Technical Report No. 254, Jan. 1996, Dept of Electrical Engineering & Computer Science, The University of Michigan, Ann Arbor, USA pp. 36–47 160–165.

Troyk et al. "Class E Driver for Transcutaneous Power and Data link for Implanted Electronic Devices" Illinois Institute of Technology, Medical & Biological Engineering & Computing, (1992), 30., pp. 69–75.

*Primary Examiner*—Scott M. Getzow
(74) *Attorney, Agent, or Firm*—McDermott Will & Emery LLP

(57) ABSTRACT

A modulated Class E transmitter is disclosed. In one embodiment of the invention, the modulated Class E oscillator achieves high coil currents (~1 A) and voltages (~500V) with low power components by precisely timed injection of current when the oscillating current in the inductor passes through zero. A detector circuit is used to trigger the current injection at the appropriate instant regardless of changes in the resonant frequency of the system. Its phase can be adjusted to compensate for propagation delays in the drive circuitry, while amplitude modulation is accomplished by switching in additional reactive conductance to increase the current injected into the tank circuit. Frequency modulation is accomplished in an alternate embodiment.

8 Claims, 6 Drawing Sheets

U.S. PATENT DOCUMENTS

| | | |
|---|---|---|
| 4,743,789 A | 5/1988 | Puskas |
| 4,814,962 A | 3/1989 | Magalhaes et al. |
| 4,833,427 A | 5/1989 | Leuthold et al. |
| 4,916,380 A | 4/1990 | Burroughs |
| 5,053,723 A | 10/1991 | Schemmel |
| 5,193,539 A | 3/1993 | Schulman et al. |
| 5,193,540 A | 3/1993 | Schulman et al. |
| 5,324,316 A | 6/1994 | Schulman et al. |
| 5,405,367 A | 4/1995 | Schulman et al. |
| 5,414,741 A | 5/1995 | Johnson |
| 5,438,302 A | 8/1995 | Goble |
| 5,486,794 A | 1/1996 | Wu et al. |
| 5,506,547 A | 4/1996 | Ishikawa |
| 5,543,754 A | 8/1996 | Onodera |
| 5,643,332 A | 7/1997 | Stein |
| 5,666,279 A | 9/1997 | Takehara et al. |
| 5,697,076 A | 12/1997 | Troyk et al. |
| 5,766,232 A | 6/1998 | Grevious et al. |
| 5,798,616 A | 8/1998 | Takehara et al. |
| 5,838,203 A | 11/1998 | Stamoulis et al. |
| 5,872,703 A | 2/1999 | Williams et al. |
| 6,016,257 A | 1/2000 | Chang et al. |
| 6,046,650 A | 4/2000 | Lichterfield |
| 6,051,017 A | 4/2000 | Loeb et al. |
| 6,064,277 A | 5/2000 | Gilbert |
| 6,073,050 A | 6/2000 | Griffith |
| 6,215,365 B1 | 4/2001 | Kurkovskiy |
| 6,225,873 B1 | 5/2001 | Hill |
| 6,229,406 B1 | 5/2001 | Wang |
| 6,239,665 B1 | 5/2001 | Strom |
| 6,255,913 B1 | 7/2001 | Wang |
| 6,268,777 B1 | 7/2001 | Welch |
| 6,275,539 B1 | 8/2001 | Kulha |
| 6,456,169 B2 | 9/2002 | Oshita et al. |
| 6,462,964 B2 | 10/2002 | Porter et al. |
| 6,469,587 B2 | 10/2002 | Scoggins |
| 6,509,805 B2 | 1/2003 | Ochiai |
| 6,538,521 B2 | 3/2003 | Kobayashi et al. |
| 6,539,253 B2 | 3/2003 | Thompson et al. |
| 6,545,554 B1 | 4/2003 | Rozenblit et al. |
| 6,553,263 B1 | 4/2003 | Meadows et al. |
| 6,593,822 B2 | 7/2003 | Nakano et al. |
| 6,593,825 B1 | 7/2003 | Washburn |
| 6,606,006 B1 | 8/2003 | Alexandersson |
| 6,614,288 B1 | 9/2003 | Dagan et al. |
| 6,621,365 B1 | 9/2003 | Hallivuori et al. |

SWITCHED REACTANCE MODULATED E-CLASS OSCILLATOR DESIGN

RELATED APPLICATIONS

This is a continuation-in-part of U.S. patent application Ser. No. 09/973,486, filed Oct. 5, 2001, which claimed priority to U.S. Provisional Application Ser. No. 60/238,488, filed Oct. 6, 2000, the content of both of which are incorporated herein by reference.

BACKGROUND OF THE INVENTION

1. Field of the Invention

This invention relates to drive coils designed to supply a powerful magnetic field to supply power and operational commands to a mismatched, spatially remote receiving coil. More particularly, the invention relates to methods and circuits for efficiently driving a resonating transmitting coil by efficient modulation of the carrier, wherein the modulation can be either amplitude modulation or frequency modulation.

2. General Background and State of the Art

Many applications require or would benefit from improved efficiency in L-C tank circuit oscillations. Achieving such efficiency, however, is problematic for a number of reasons. Such problems may be illustratively presented in the context of a particular, exemplary application. Therefore, although there are many applications which would benefit from an efficiently driven oscillator, the description herein will continue with particular reference to a single exemplary application involving BIOnic Neurons (BIONs).

BIONs are implantable micromodular electrical stimulators that can be located internally within a body. Specifically, BION implants may be placed in or near nerves or muscles to be electrically stimulated. BIONs comprise elongated devices with metallic electrodes at each end that deliver electrical current to immediately surrounding biological tissues. The implantable electronic devices are hermetically sealed capsules having the metallic electrodes attached thereto, and containing electronic circuitry therein. BION implants are about 100 times smaller in volume than conventional implantable electronic devices such as cardiac pacemakers and cochlear implants, resulting in significant physical limits on the general principles of power, data transmission and packaging fundamental to operation of BIONs.

The microelectronic circuitry and inductive coils that control the electrical current applied to the electrodes are protected from body fluids by the hermetically sealed capsule and, additionally, can be covered with a biocompatible coating or sheath for further protection of the capsule. The electronic circuitry typically includes an inductive coil, power storage capacitor, and integrated circuit for performing various functions.

Upon command from an external component, the implanted BION emits an electrical stimulation pulse that travels through the body tissues between and around its electrodes, thereby activating, for example, local nerve fibers as required for particular treatments. The BION microstimulator receives power and control signals by inductive coupling to an externally generated RF magnetic field, which is a practical method for recharging a BION's battery and controlling the timing and parameters of stimulations generation by the BION. This is achieved by inductive coupling of magnetic fields generated by extracorporeal antenna and do not require any electrical leads, as discussed in U.S. Pat. Nos. 5,193,539, 5,193,540, 5,324,316, 5,405,367, and 6,051,017, incorporated herein by reference. By selecting the appropriate strength and temporal patterning of stimulation, a desired therapeutic effect can be achieved.

Unfortunately, the small, narrow shape of BIONs has resulted in stringent requirements for wireless power and data transmission and electromechanical assembly. Developing solutions to meet these requirements has been difficult.

For example, the inductive coupling between a primary inductive coil within an extracorporeal antenna utilized to power a BION and a small, secondary inductive coil within the BION itself is difficult to establish and maintain within the stringent requirements of the BION's power, data transmission, and electromechanical assembly. One reason for this is that the coefficient of inductive coupling between a large primary coil and a distant, small secondary coil across an air gap is very low, typically less than 2%. Therefore, the BION must be assembled such that the length and the cross-sectional area of its receiving coil are maximized. However, the very nature of the BION's necessarily small size establishes strict limits on the BION's receiving coil size.

To compensate for the necessarily weak coupling coefficient which thus results, the strength of the primary RF magnetic field, generated by the extracorporeal antenna, for example, must be made high without incurring excessive power dissipation. Specifically, the extracorporeal antenna must be driven to at least 200–400V, and more ideally, to 500V, in order to generate sufficient power to drive the remote, implanted BION. However, selection of an appropriate oscillator to generate sufficient field strength has been problematic. It will be appreciated by those skilled in the art, of course, that the exemplary application discussed herein, involving BIONs, provides one context only, in which efficiently powered oscillators would provide significant improvement, and it will be readily apparent to those skilled in the art that a number of other applications would also be substantially improved by such an oscillator.

As is well understood in the art, power oscillators are classified according to the relationship between the output voltage swing and the input voltage swing. Thus it is primarily the design of the output stage that defines each class. Specifically, classification is based on the amount of time the output devices operate during one complete cycle of signal swing. This is also defined in terms of output bias current, or the amount of current flowing in the output devices with no applied signal.

Conventional A-Class amplifiers are not efficient enough for field use, as they exhibit significant power dissipation. An alternative choice is an E-Class amplifier, or E-Class oscillator. Class E operation involves oscillators designed for rectangular input pulses, not sinusoidal waveforms. The output load is a tuned circuit, with the output voltage resembling a damped single pulse. Advantageously, a Class-E oscillator operates in a switched mode (ON or OFF) which provides a very high collector efficiency that can theoretically approach 100%. In operation, the energy content, or drive level, of the inter-stage signal applied to such single RF transistor, in combination with a temperature-compensated bias circuit, is optimally set so that the single RF transistor is always sufficiently driven ON or OFF with each cycle of the inter-stage signal, but is not overdriven ON or OFF. Although the high field strength and low power dissipation requirements of BION applications, in, general, might be accomplished by using a Class E amplification with a very high Q (>100) tuned circuit, it has been unclear how to effectively utilize a Class E oscillator in a BION application, because of the BION's two other previously mentioned requirements: power efficiency and data transmission.

These requirements are fundamentally in conflict, as power efficiency requires highly resonant operation of the Class E oscillator, while data transmission requires rapid amplitude modulation of the Class E oscillator. With respect to the rapid amplitude modulation in particular, a problematic feature of the Class E oscillator, in BION applications, is that both the position and duration of the drive pulse are critical. For a coil frequency of 2 MHz, any drive pulse over 125 ns causes excessive power dissipation in the switch without significantly increasing the energy in the coil. However, producing various pulse widths requires additional components that increase the cost and size of the coil driver assembly, which is impractical in BION applications.

In addition to these complications, using a Class E oscillator in BION applications causes additional problems. For example, the flexible shape of the BION may easily be deformed while it is worn by the patient. Such deformities will cause fluctuations in the inductance of the external coil, and a Class E oscillator does not inherently accommodate such fluctuations. Moreover, the electromechanical assembly requirements of BIONs make it desirable to accommodate the driver circuitry on the coil itself. This type of construction makes a typical Class E oscillator unsuitable for BION applications. Further, complicated circuitry is required to change pulse width for achieving desired AM modulation, when utilizing a typical Class E oscillator. Changes in pulse width are undesirable because they cause significant degradation of efficiency, something a battery-operated BION has limited capacity to endure.

Of course, it is again emphasized that while the description herein continues in the context of BIONs as an illustrative mechanism, BIONs are an exemplary application only, and a number of other applications, such as radio communication, metal detectors, mine detection, or power and data transmission to many types of remote devices, would also benefit greatly from an oscillator having an efficient driving mechanism greater than that available in standard Class E oscillators.

INVENTION SUMMARY

The present invention overcomes these, and other, problems by providing novel oscillator designed to accommodate the stringent requirements of BIONs as discussed above. More specifically, the present invention involves a novel Class E modulated transmitter capable of compensating for the weak coupling coefficient between a BION's receiving coil and the corporeal antenna's primary coil, accommodating fluctuations in the inductance of the external coil that arise when the BION's flexible shape is deformed while being worn by a patient, providing highly resonant operation for power efficiency, and providing rapid amplitude modulation to transmit data from the BION.

In one embodiment of the invention, the novel Class E oscillator achieves high coil currents (~1 A) and voltages (~500V) with low power components by precisely timed injection of current when the oscillating current in the inductor passes through zero. A detector circuit is used to trigger the current injection at the appropriate instant regardless of changes in the resonant frequency of the system. Its phase can be adjusted to compensate for propagation delays in the drive circuitry, while amplitude modulation is accomplished by switching in additional reactive conductance to increase the current injected into the tank circuit. Again, it is emphasized that various embodiments of the present invention may be utilized in a variety of applications including, but not limited to, radio communication using amplitude modulation or frequency modulation, high efficiency coil driving for portable devices such as metal detectors or mine detection, or power and data transmission to remote devices such as medical devices implanted in patients.

In a still further embodiment, frequency modulation is accomplished.

The foregoing and other objects, features, and advantages of the present invention will be become apparent from a reading of the following detailed description of exemplary embodiments thereof, which illustrate the features and advantages of the invention in conjunction with references to the accompanying drawing Figures.

DETAILED DESCRIPTION OF THE PREFERRED EMBODIMENTS

In the following description of the preferred embodiments reference is made to the accompanying drawings which form the part thereof, and in which are shown by way of illustration specific embodiments in which the invention may be practiced. It is to be understood that other embodiments may be utilized and structural and functional changes may be made without departing from the scope of the present invention.

Figure 1:
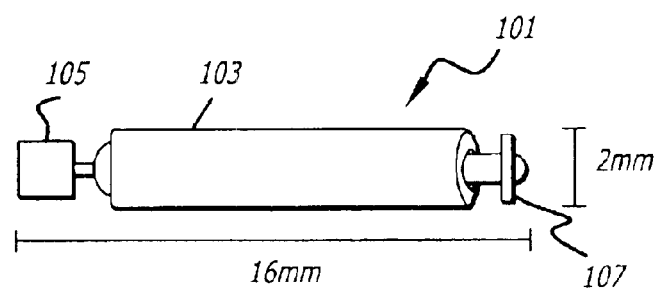
FIG. 1 illustrates an exemplary design and fabrication of a BION microtransmitter implant.

FIG. 1 illustrates a BION 101 and its typical size. Encased in a glass sheath 103 and having two electrodes, a Ta electrode 105 and an Ir electrode 107, BION 101 has a typical size of 2 mm in diameter and 16 mm in length. The small size is important, because it allows BIONs to be implanted by injection in an outpatient procedure that can be performed by any physician. Further, their small size allows them to be placed in small, deep, or hard-to-reach muscles that are impossible to stimulate selectively from the skin surface. Further, the small size and wireless nature of implantable BIONS minimizes threat of infection, skin breakdown, and tissue damage, which are concerns related to other types of implants that are either too large, particularly in areas where multiple implants were required, or have many long leads.

Figure 2:
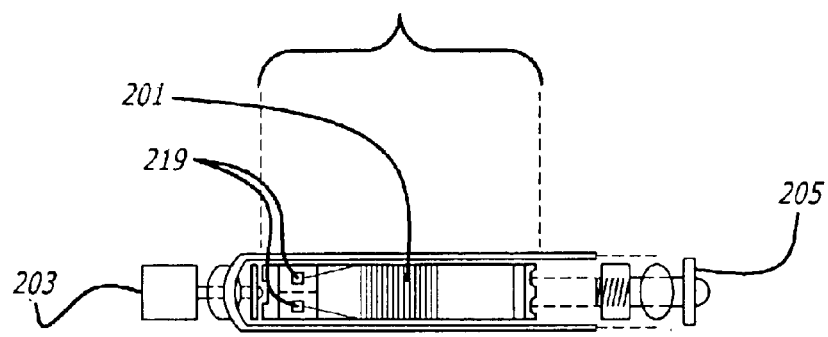
FIG. 2 illustrates a capsule subassembly component of the BION illustrated in FIG. 1.
Figure 3:
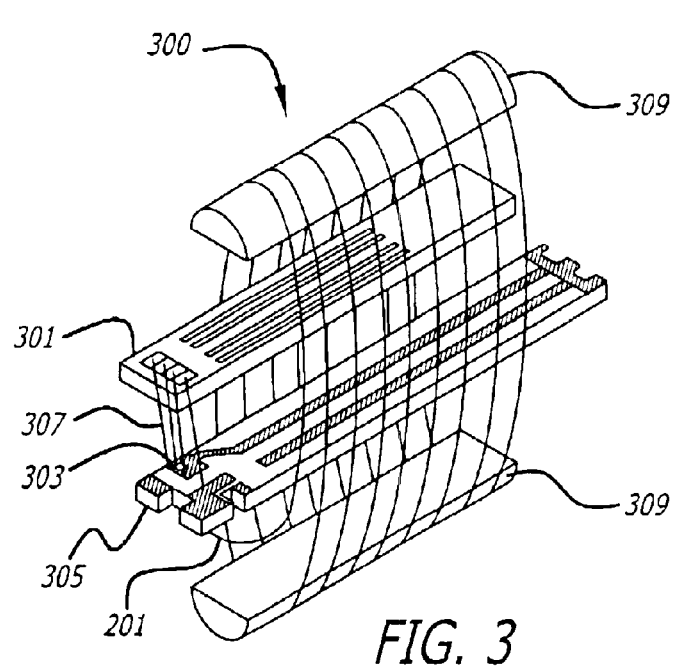
FIG. 3 illustrates an exploded view of an electronic subassembly component of the BION illustrated in FIG. 1.

FIGS. 2 and 3 illustrate electronic circuitry in an exemplary BION. As shown in FIG. 2, a self-resonant receiving coil 201 is located between two electrodes: a capacitor electrode 203 and a counter electrode 205. FIG. 3 shows that receiving coil 201 is wound about an integrated circuit chip (IC) 301, a diode chip 303 such as, for example, a Schottky diode, and two semihylindrical ferrites 309. IC 301 derives DC power by rectifying and filtering carrier energy picked up by receiving coil 201. The carrier itself provides a synchronous clock and its amplitude modulations encode a serial bit stream, which is decoded by a state machine in IC 301. The first data byte specifies an address, which is compared to an address specified by a hardwired read-only memory in IC 301. If the addresses match, subsequent data bytes are decoded to specify the desired operation of the BION. In an exemplary embodiment, stimulation operations require a pulse width and a pulse amplitude specification, which are contained within the encoded serial bit stream received by receiving coil 201 and encoded by IC 301.

Stimulation typically required to activate a muscle comprises relatively brief pulses, such as 0.2 ms, for example, at low frequencies, such as less than 20 pps, for example. During the interpulse period, which is, for example, typically greater than 50 ms, energy is stored in an electrolytic capacitor. Continuing with FIG. 2, the electrolytic capacitor comprises the combination of capacitor electrode 203 and body fluids. Counter electrode 205 resists polarization under all sequences of charging and discharging of capacitor electrode 203. When the carrier is on but the implant is idling, capacitor electrode 203 can be charged until it becomes fully polarized. In the exemplary embodiment described herein, this charging can be accomplished at one of four selectable rates (0 $\mu$A, 10 $\mu$A, 100 $\mu$A and 500 $\mu$A) and full polarization is achieved at approximately +17 VDC compliance voltage.

In contrast to stimulation functions, sensing functions require a back-telemetry link that operates during pauses in the external carrier, during which an external coil, worn by the patient, acts as a receiving antenna. Self-resonant coil 201 in the BION acts as the tank circuit for an oscillator that is amplitude modulated to transmit digitized data obtained from a previously commanded sensing operation. Three sensing modalities are contemplated within the scope of the present invention. A Bioelectrical recording sensing modality utilizes voltages present on electrodes 203 and 205 that can be amplified, integrated and digitized according to gain and timing programmed by the command that initiates the sensing operation. Such data might represent the impedance of the tissue through which a current pulse is being delivered simultaneously, the electrical field created in the tissue by a stimulus pulse from another implant, or a bioelectrical signal such as electromyographical activity. An acceleration sensing modality incorporates microelectromechanical silicon systems (MEMS) into the BION to sense acceleration or inclination with respect to the gravitational field of the BION implant. A relative position sensing modality utilizes the dependence of a detected signal on the distance and relative orientation between emitting and detecting BIONS. Changes in a patient's limb posture produce relative motion of BIONS located in the patient's various muscles, permitting limb posture and motion to be inferred from a set of coupling strengths among several implanted BIONS.

Proceeding with FIG. 3, electronic subassembly 300 comprises a ceramic two-sided microprinted circuit board ($\mu$PCB) 305, which provides a mechanical platform for the inside of electronic subassembly 300 and makes all of the electrical interconnections on both surfaces and ends. On one side, $\mu$PCB 305 carries IC 301, diode chip 303, and their conventional gold wirebonds 307 to substrate $\mu$PCB 305 which may be, for example, alumina. The hemicylindrical ferrites 309 are glued to the top and bottom surfaces of subassembly 300, and self-resonant coil 201 is wound over the ferrites 309 and solder-terminated to the back of $\mu$PCB 305. Although not illustrated in FIG. 2 and FIG. 3, self-resonant coil 201 has approximately 200 winds. Solder terminations 219 are visible in FIG. 2.

BION 101 receives commands and sends signals through RF power and communications supported by the novel E-Class oscillator design of the present invention. BION 101 draws very little power, but does so by inductive coupling between its receiving coil 201 and a wearable, primary coil worn by a patient. The two coils have a very low coupling coefficient, such as less than 3%, due to their physical separation and mismatch in size. Such a low coupling coefficient requires an intense RF magnetic field for power and communications, such as 1 A at 500V peak in the wearable, primary coil, which is, in the exemplary embodiment, 4–6 turns of 18 ga stranded wire.

In order to generate the strong magnetic field efficiently, the novel oscillator of the present invention utilizes a very high Q tank circuit comprising the wearable, primary coil and a small tuning capacitor which has, in the exemplary embodiment, a Q of ~100. By switching in the capacitor, the reactance of the primary coil can be changed, eliminating the need for prior art methods involving complicated circuitry to change pulse width for achieving desired AM modulation. As described earlier, changes in pulse width are undesirable because they cause significant degradation of efficiency.

The novel oscillator injects a brief current pulse into the tank circuit only at the time when the current through the wearable, primary coil is passing through zero and the voltage across the driving Metal-Oxide-Semiconductor Field-Effect-Transistor (MOSFET) of the E-Class oscillator is at its negative peak, which is ground in the novel oscillator circuit.

The novel oscillator circuit further comprises a feedback circuit, comprising an adjustable phase shift and zero-crossing detector which compensates for propagation delays in drive circuitry, as well as shifts in resonant frequency that may result from deformation of the coil such as when the patient moves. All reactive components utilized in embodiments of the present invention are preferably selected to minimize dissipation and could include, for example, silver mica capacitors, highly stranded antenna wire, and very fast transistors.

Figure 4:
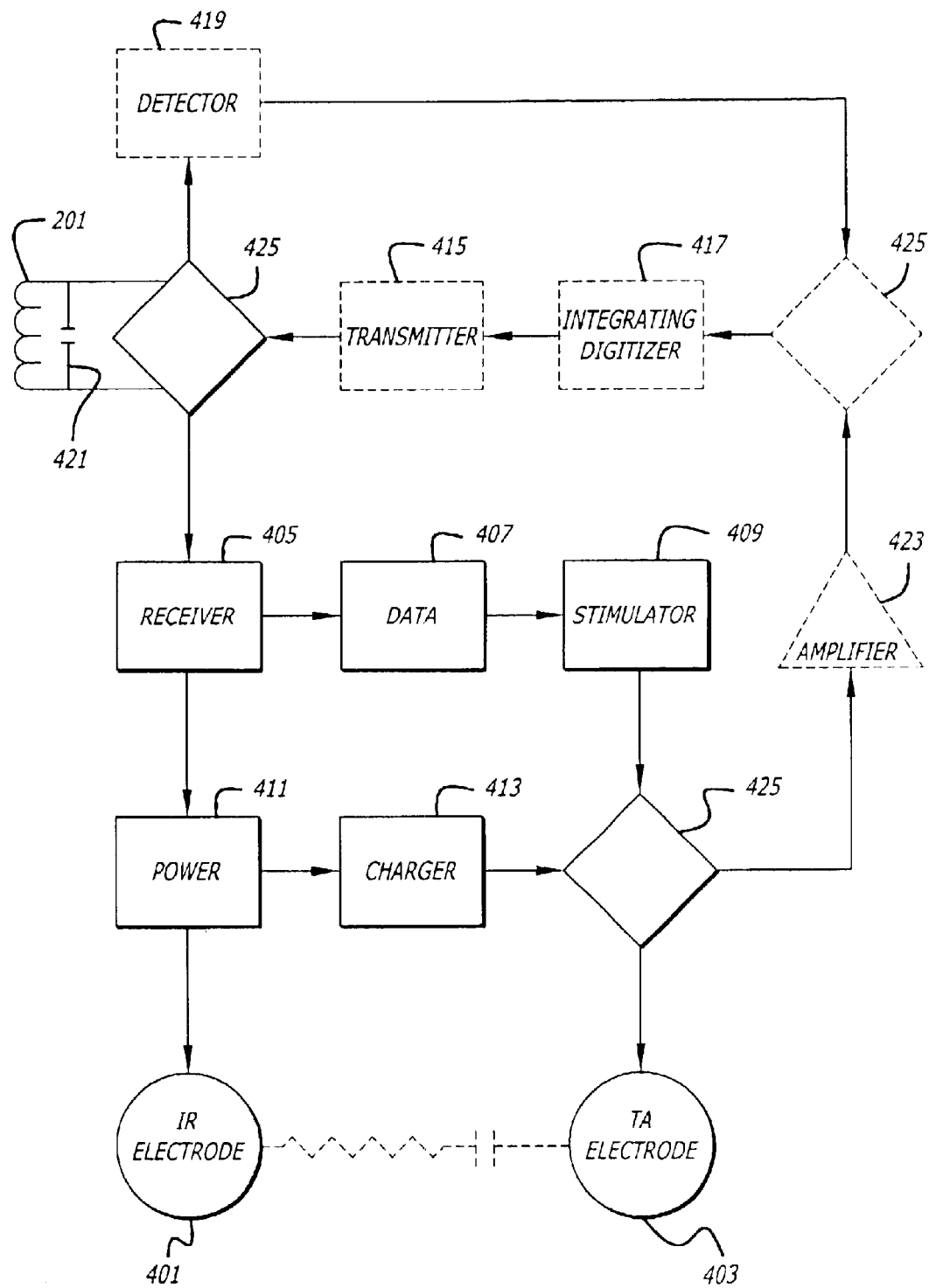
FIG. 4 illustrates internal, implantable components of an exemplary BION system architecture.
Figure 5:
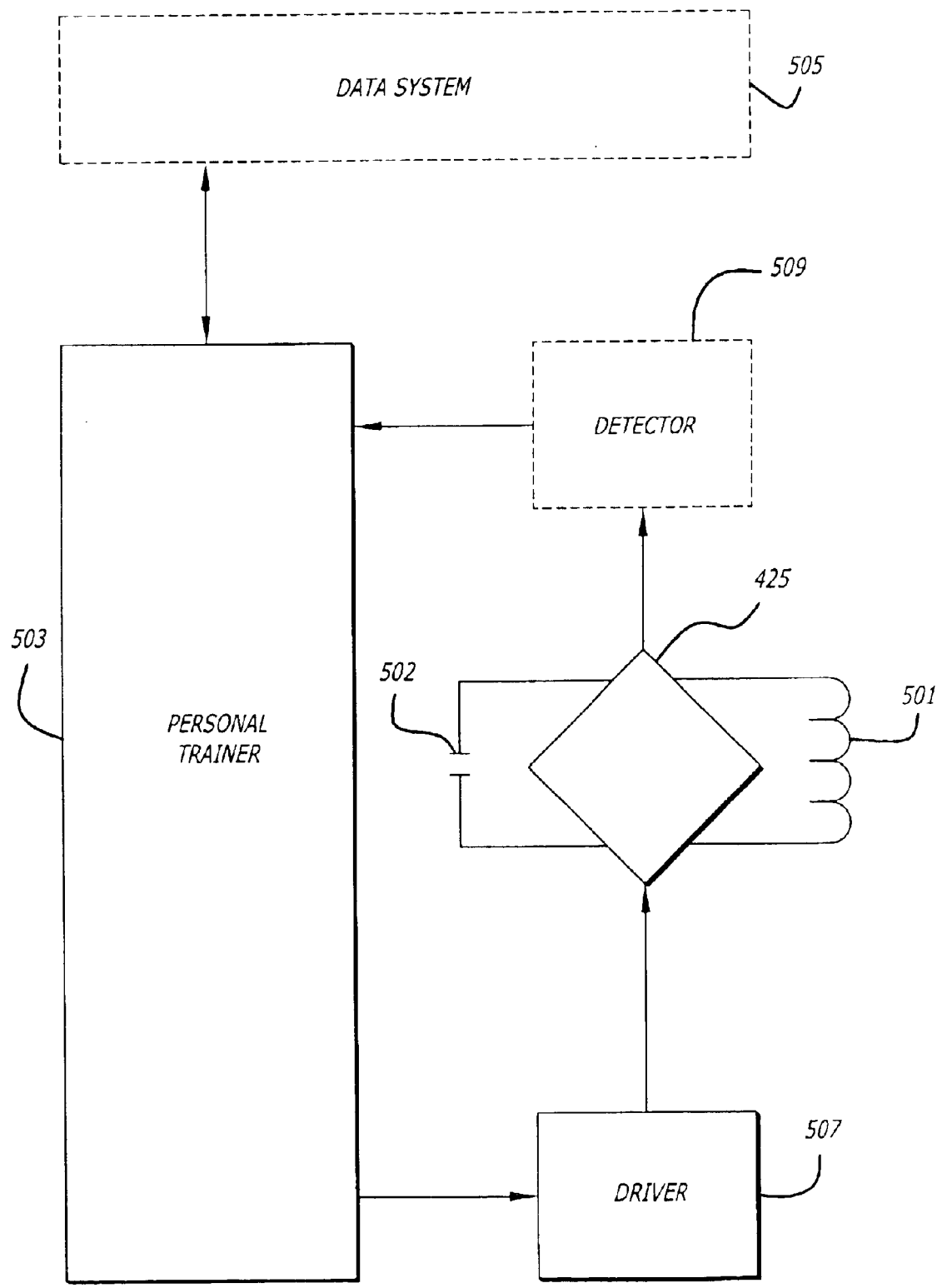
FIG. 5 illustrates external components of the exemplary BION system architecture of FIG. 2.

FIG. 4 and FIG. 5, together, illustrate an exemplary BION system architecture. FIG. 4 and FIG. 5 are directed to the internal circuitry of an implantable BION and to the external circuitry involving the wearable, primary coil, respectively. Power and communication transmissions occur between the internal and external circuitry through a patient's skin and, specifically, is achieved by inductive coupling between self-resonant coil 201 in FIG. 4 and a magnetic field generated by wearable, primary coil 501 in FIG. 5.

FIG. 4 illustrates functions of electronic subassembly 301. Capacitor electrode 401 and counter electrode 403 transmit signals from electronic subassembly 301. As illustrated in the block diagram of FIG. 5, electronic subassembly 301 receives data at block 405, decodes data at block 407, and creates a stimulating charge, at block 409. Additionally, electronic subassembly 301 provides power at block 411 and generates charge at block 413. A feedback circuit includes an integrating digitizer, at block 415, a transmitter at block 417, and an adjustable phase shift and zero-crossing detector at block 419. A tuning capacitor 421 is also included in the feedback circuit. Once a stimulating charge has been determined at block 409, it is amplified if necessary at block 423. Multiple blocks 425 represent switching functions.

FIG. 5 illustrates external components of BION systems that can be utilized with an efficient modulated Class E oscillator according to the present invention. The wearable, primary coil described above is transmission coil 501. The resonant frequency of the tank circuit of the novel oscillator design of the present invention is set by transmission coil 501 and capacitor 502. Transmission coil 501 is sized and shaped for the body part to be stimulated, and has an integral small enclosure for its tuned RF power circuitry that connects to and is controlled by personal trainer 503. Personal trainer 503 functions like a very large, externally synchronized shift register to produce previously stored sequences of carrier modulations that activate the patient's various BION implants. For example, in the exemplary embodiment, personal trainer 503 comprises a 68HC11 microcontroller with battery-backed RAM, powered by a conventional AC-DC converter that plugs into an AC power outlet. A clinician uses a personal computer to load exercise programs into personal trainer 503, which converts those programs into sequences of amplitude modulation of the 2 MHz carrier. Transmission coil 501 generates the 2 MHz magnetic field that powers and commands the BION functions with commands as described above. An internal microcontroller, within personal trainer 503, monitors, timestamps and records all usage of its programs by a patient. These data are then uploaded to a data system 505 when a patient has completed a personal trainer program, and the data system adjusts stimulation parameters for follow-up treatment, if necessary.

Figure 6:
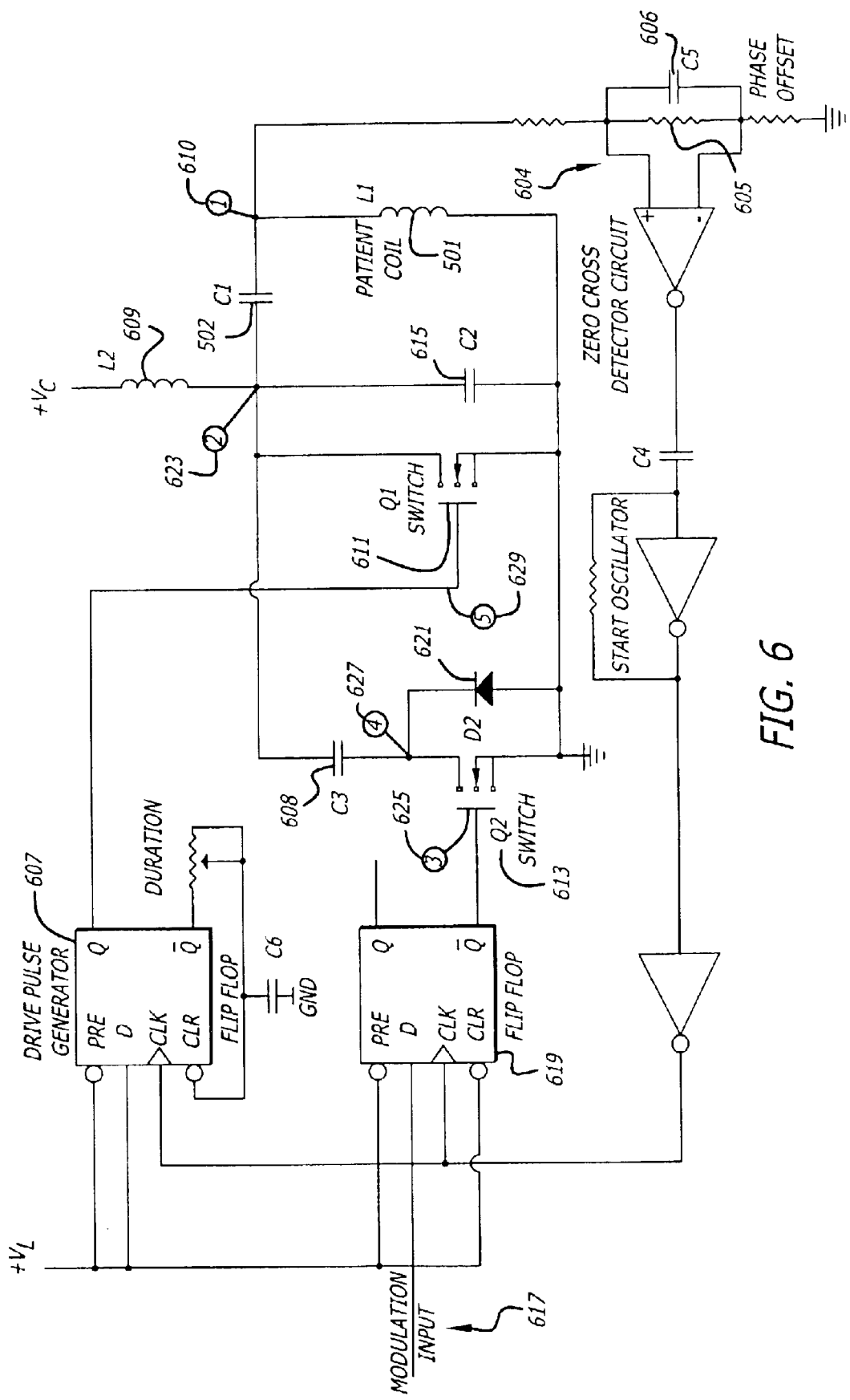
FIG. 6 illustrates an exemplary Class E modulated power oscillator circuit utilized in one embodiment of the invention.
Figure 7:
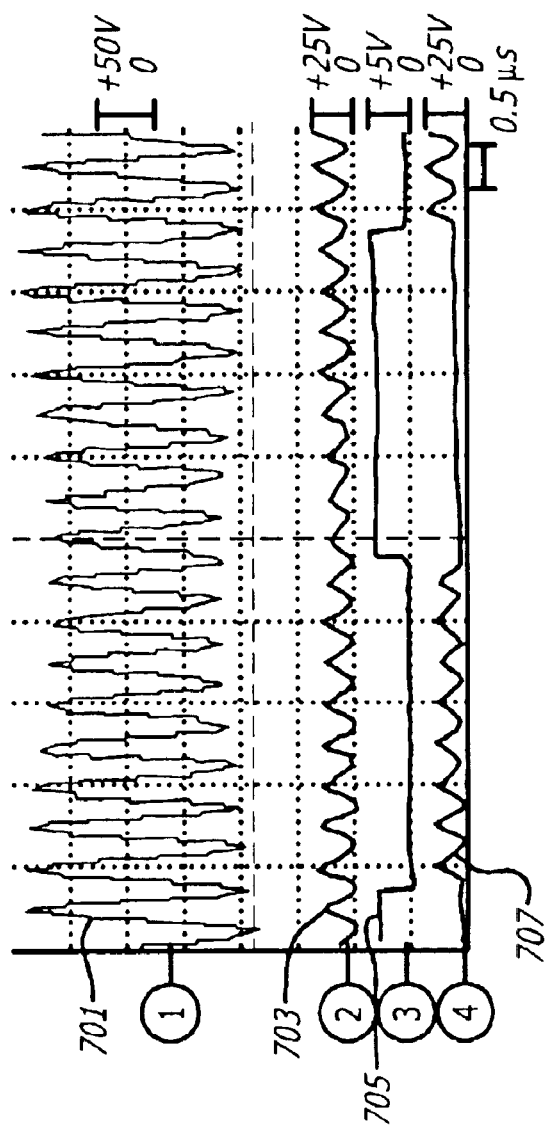
FIG. 7 illustrates exemplary waveforms at various test points in the circuit illustrated in FIG. 6.
Figure 7:
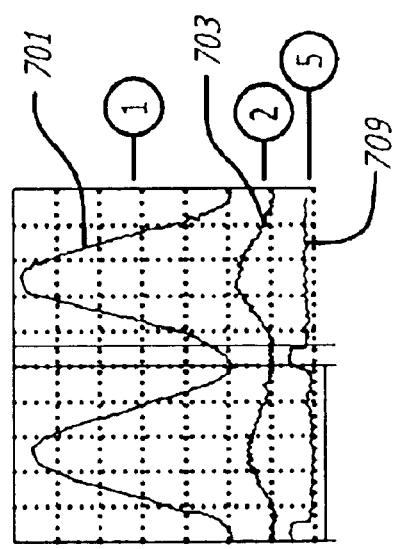

FIG. 6 illustrates an exemplary schematic for the novel oscillator design of the present invention. The novel design includes circuitry for modifying a Class E oscillator with switched reactance modulation. As will be apparent to those skilled in the art, the resonant frequency of the tank circuit may be set by transmission coil 501 (worn by the patient) and capacitor 502, which were previously introduced in the overall system design depicted in FIG. 5. The zero-crossing of the current on the inductor is detected by zero cross detector circuit, shown generally at location 604. Specifically, the zero-crossing is detected across resistor 605—capacitor 606, whose phase can be adjusted to assure that drive pulse generator 607 fires for a preset duration that straddles the time when the voltage across the MOSFET is minimal and power injection is most efficient. Modulation is accomplished by switching in parallel capacitor 608, which increases the current drawn into the tank circuit through choke 609, in turn increasing the amplitude of the oscillations to a new steady state over about four carrier cycles. These oscillations are measured at test point 1, indicated at location 610 by a test point indicator marked as an encircled numeral. This test point indicator, as well as four others (marking test points 1 through 5) correspond to the waveforms shown in FIG. 7. Specifically, signal 701 in FIG. 7 corresponds to test point 1, indicated at 610 in FIG. 6; signal 703 in FIG. 7 corresponds to test point 2, indicated at 623 in FIG. 6; signal 705 in FIG. 7 corresponds to test point 3, indicated at 625 in FIG. 6; signal 707 in FIG. 7 corresponds to test point 4, indicated at 627 in FIG. 6; and, signal 709 in FIG. 7 corresponds to test point 5, indicated at 629 in FIG. 6. As will be appreciated by those skilled in the art, these waveforms are exemplary of the functioning novel oscillator circuit of the present invention.

Further describing the novel switched reactance modulated oscillator circuit of the present invention, it is notable that the exemplary circuit illustrated in FIG. 6 uses a technique that requires only one pulse width of ideal duration. Switched reactance modulation is the technique used to encode data on the carrier. Specifically, as it applies to the present invention, switch 611 provides a fixed drive pulse. When switch 613 is open, capacitor 608 is not in the series resonant path and the sine wave voltage at the junction of transmission coil 501 and capacitor 503 is at some present minimum defined by the losses in the tank circuit versus the regenerative current pulses, whose amplitude depends on the value of capacitor 615. When switch 613 is closed, on the other hand, capacitor 608 is in the series resonant path, providing additional capacitance in parallel with capacitor 615 and increasing the injected current, which in turn increases the amplitude of the oscillations in the tank circuit.

Modulation Input 617 is applied through flip flop 619 to synchronize changes in the state of MOSFET switch 613 (test point trace 3) with the zero current points detected by feedback circuit 604. Diode 621 provides the current charge path from ground to capacitor 608 (test point 4). The current discharge path is provided by MOSFET 613. When MOSFET 613 is turned off, capacitor 608 is, in effect, removed from the circuit. As will be appreciated by those skilled in the art, by using various values for the ratio of capacitor 615 to capacitor 608, the same circuitry can be used to generate primarily frequency modulation rather than amplitude modulation.

Figure 8:
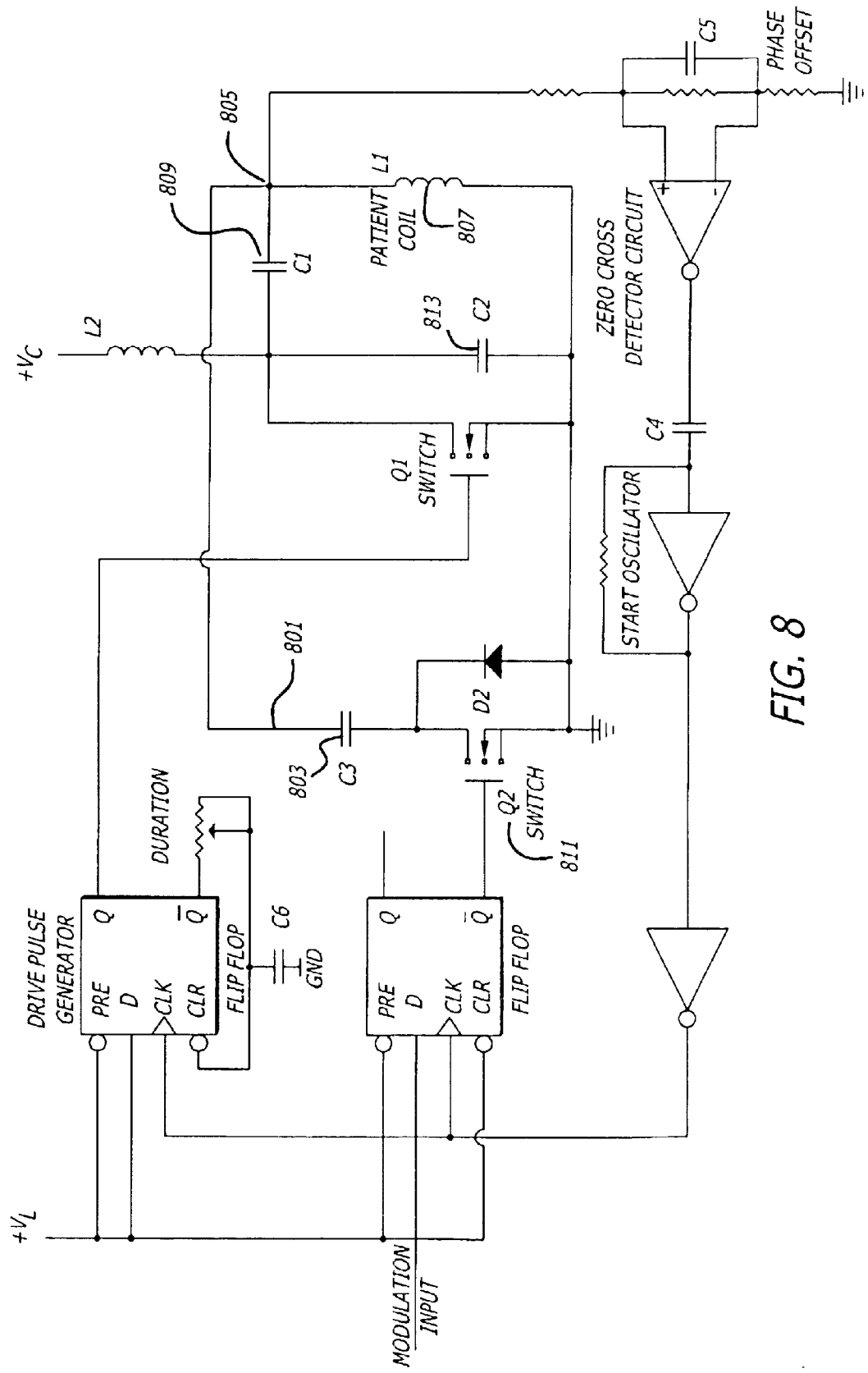
FIG. 8 illustrates an exemplary Class E modulated power oscillator circuit utilized in another embodiment of the invention that provides frequency modulation.

FIG. 8 illustrates an exemplary Class E modulated power oscillator circuit utilized in another embodiment of the invention that advantageously provides frequency modulation. This embodiment is identical to the one shown in FIG. 6 and operates in the same way, with one notable exception. One of the connections 801 to capacitor 803 is connected to the junction 805 between the patient coil 807 and tank capacitor 813. When connected in the circuit by switch 811, the capacitor 803 is effectively placed in parallel with the patient coil 807. With appropriate values for the capacitors, this alternate embodiment causes the oscillations to be frequently modulated by the modulation input, rather than amplitude modulated. Although frequency modulation can also be effectuated through the selection of appropriate values of the capacitors in the circuit shown in FIG. 6, the configuration shown in FIG. 8 is believed to provide superior results.

It is, of course, to be understood that numerous values could be chosen for the capacitors and coil in the circuits shown in FIGS. 6 and 8. The following values are known to work: capacitors 608 and 803: 680 pf; capacitors 615 and 813: 2700 pf; capacitors 502 and 809: 680 pf; coils 501 and 807: 10 uh.

The foregoing description of the preferred embodiments of the invention has been presented for the purposes of illustration and description. It is not intended to be exhaustive or to limit the invention to the precise form disclosed. Many modifications and variations are possible in light of the above teaching. For example, a variety of alternative components may be utilized in the novel oscillator design of the present invention, as will be recognized by those skilled in the art, to build an oscillator that functions according to the teachings herein. It is intended that the scope of the invention be limited not by this detailed description, but rather by the claims appended hereto.

What is claimed is:

1. A switched reactance modulated E-class oscillator comprising:

a tank circuit including an inductance and a capacitance for helping to generate an oscillating signal;

a zero crossing detector in communication with said tank circuit for detecting zero crossings of the oscillating signal;

a drive pulse generator in communication with said tank circuit and said zero crossing detector for injecting injection signals into said tank circuit in response to zero crossings detected by said zero crossing detector;

a reactance;

an electronic switch; and a modulator in communication with said electronic switch for receiving a modulating signal and for causing said tank circuit to be loaded with said reactance in synchronism with the modulating signal using said electronic switch;

whereby the oscillator operates substantially in the E-class mode.

2. The oscillator of claim 1 wherein:

said tank circuit is a series resonant tank circuit;

said reactance includes substantial capacitive reactance; and said inductance and said capacitance are connected in series.

3. The oscillator of claim 2 wherein:

said capacitance includes two capacitors connected in series;

said switch causes said capacitive reactance to be added in parallel with one of said capacitors; and said modulator causes substantial amplitude modulation.

4. The oscillator of claim 2 wherein:

said switch causes said capacitive reactance to be added in parallel with said inductor; and said modulator causes substantial frequency modulation.

5. A source of power and control signals for an implanted BION comprising:

a tank circuit including an inductance and a capacitance for helping to generate an oscillating signal, said inductance forming a coil that acts as an antenna for radiating the power and control signals;

a zero crossing detector in communication with said tank circuit for detecting zero crossings of the oscillating signal;

a drive pulse generator in communication with said tank circuit and said zero crossing detector for injecting injection signals into said tank circuit in response to zero crossings detected by said zero crossing detector;

a reactance;

an electronic switch; and a modulator in communication with said electronic switch for receiving a modulating signal and for causing said tank circuit to be loaded with said reactance in synchronism with the modulating signal using said electronic switch;

whereby the oscillator operates substantially in the E-class mode.

6. The oscillator of claim 5 wherein:

said tank circuit is a series resonant tank circuit;

said reactance includes substantial capacitive reactance; and said inductance and said capacitance are connected in series.

7. The oscillator of claim 6 wherein:

said capacitance includes two capacitors connected in series;

said switch causes said capacitive reactance to be added in parallel with one of said capacitors; and said modulator causes substantial amplitude modulation.

8. The oscillator of claim 6 wherein:

said switch causes said capacitive reactance to be added in parallel with said inductor; and said modulator causes substantial frequency modulation.

\* \* \* \* \*